July 25, 1933. F. SCHRAMM Plant Pat. 72
PINK ROSE
Filed Jan. 20, 1933
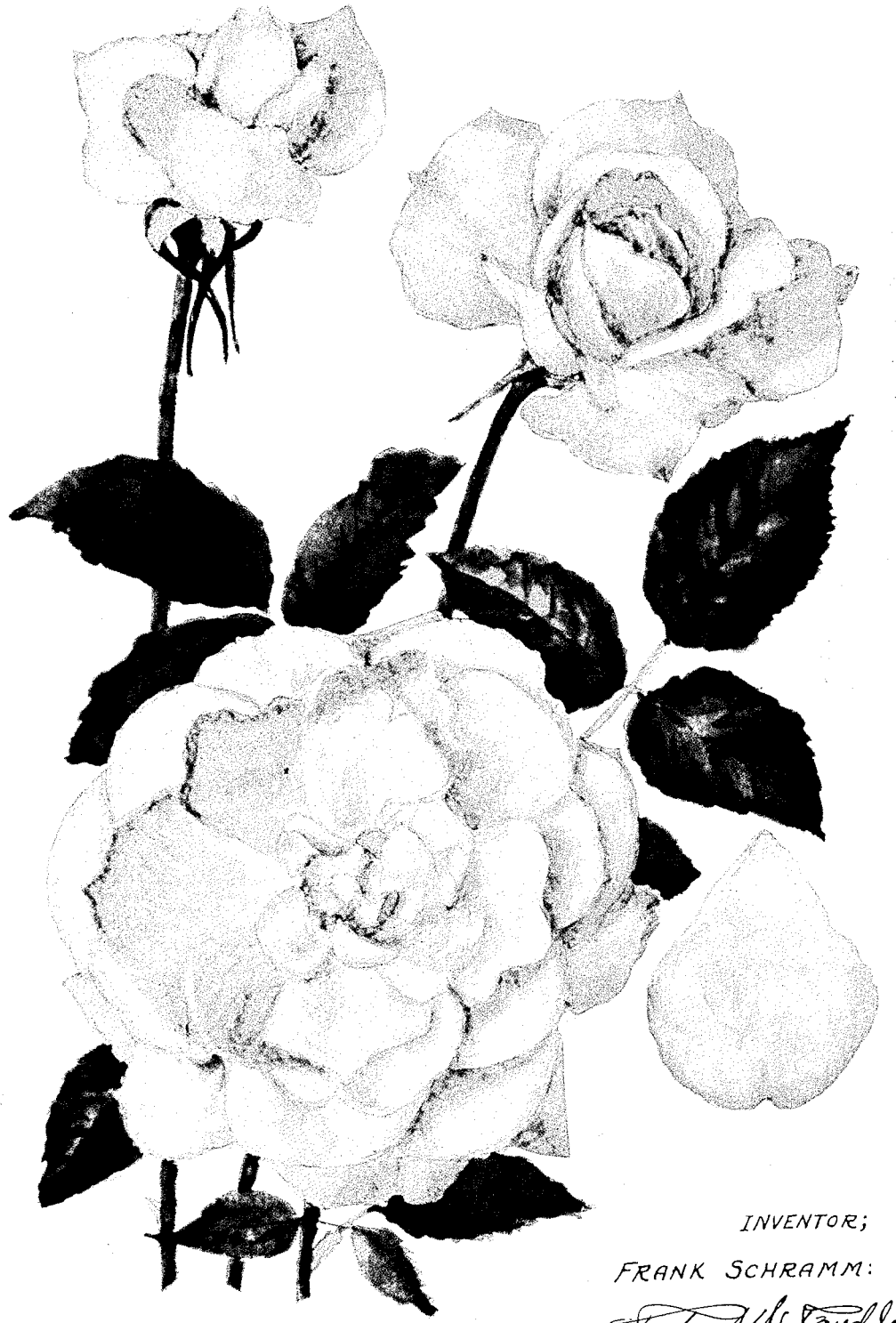
INVENTOR;
FRANK SCHRAMM:
Robert B. Caudle
ATTORNEY.

Patented July 25, 1933

Plant Pat. 72

UNITED STATES PATENT OFFICE

FRANK SCHRAMM, OF CRYSTAL LAKE, ILLINOIS

PINK ROSE

Application filed January 20, 1933. Serial No. 652,713.

Some of the more dominant features of my new rose are shown in the accompanying illustration thereof, which forms an integral part of this specification, but manifestly it can not do justice to the natural colorature of my rose, neither can the voluminosity of its flavor, or the lasting extent of its fragrance, be shown artificially.

This application relates, primarily, to the production of a new and distinct variety of flowers, of the genus "rosa," which is unique in character, delectable in appearance, and which has a colorature which is particularly pleasing to ones sight.

Another important feature which I have developed in my new rose resides in its aroma, which is of unusually attractive, delicate, and lasting fragrance.

And, concomitant with the above, I have produced a very attractive foliage comprising large dark-green pinnated leaves, accompanied by large and stiff peduncles of relative great length, capable of properly supporting the large bloom at an unusual great height. And, still another important feature of my rose resides in the prolificness thereof, and in its ease of propagation, and in the fact that the periphery of each bloom usually measures five and one-fourth inches in diameter.

I have determined that all of the qualities, above mentioned, have become permanently fixed, and also I have definitely ascertained that it is fully 20% stronger in growth, constitution, and productiveness, over that of its parent plant: "Briarcliff".

Referring to the illustration, forming a part of this specification, there is shown a full-blown rose, as it would appear when looking directly into the face thereof; also showing a partly open bloom; and an undeveloped bud; also showing a single petal as detached from a bloom.

The prima facie impression one gets when first viewing one of my new roses, is that it is composed of a single color, but upon a closer and more minute inspection thereof, one will find that while the color of the petals are a bright glowing rosepink, yet the extreme inner end portions thereof, are a light yellow color, thereby forming the inner corolla of a yellowish cast. Also the pistils are a light lemon yellow. The stamens are a dark yellow, while on the outer terminals of the stamens are formed the dark brown anthers, or stigmas. The sepals forming the calyx, are long and pointed, directed downwardly when the bloom has matured, and they are of a delicate light green in color. The leaves are pinnated, and are of an unusually large size, and are of a very dark green color. And the stems, or peduncles, are large and very strong, and they are of exceedingly great length.

A tang of especial distinction is given to my new rose, by reason of its extra large and voluminous bloom, its harmonious combination of delicate colors, its attractive leaves, and its unusually long and stiff peduncles, capable of supporting the large bloom in a distinctive manner, the ensemble giving the entire plant a semblance of predominating superiority and an ecstatic beauty.

The grounds for the resultant beauty and dignity of my new rose, seems to be in certain inbred contents which are inherent in the natural ensemble.

My rose, in this instance, originated as a sport of a Briarcliff rose, since which I have propagated it several times, both by budding and by grafting, and it has come true each time to its original colors and characteristics, and with distinct improvements in the good qualities herein mentioned. During all of the time I have been propagating this rose not one of the blooms has reverted backwardly toward its original stock, and not even deteriorated in its appearance, or other desirable qualities above mentioned.

My new rose, herein shown and described, has been asexually reproduced prior to this application for patent, and it has been brought to its present perfected status of reproduction, within the last two years, and I believe that its characteristics herein set forth, have been demonstrated to be susceptible of asexual reproduction upon a commercial scale.

What I particularly claim, in this instance, is:

The exclusive right to reproduce a new and distinctive variety of roses, substantially as that herein shown and described, characterized particularly by its very large bloom of unusual depth and large petals, its bright glowing rosepink colorature uniformly throughout the extent of the petals, except at their inner ends, having a tinge of yellow forming its inner corolla, its dark-green pinnated leaves, its very long and strong peduncles, its free and strong-growing qualities, the prolificness of its bloom, its ease of propagation, and its ability at all times to emit an aroma of delicate and lasting fragrance of great extent.

FRANK SCHRAMM.